(12) United States Patent
Rilhac et al.

(10) Patent No.: US 11,872,303 B2
(45) Date of Patent: Jan. 16, 2024

(54) **OIL EXTRACT FROM *GARDENIA JASMINOIDES* FLOWERS AND COSMETIC COMPOSITIONS COMPRISING IT**

(71) Applicant: CHANEL PARFUMS BEAUTE, Neuilly sur Seine (FR)

(72) Inventors: Vincent Rilhac, Neuilly sur Seine (FR); Maeva Gillet, Neuilly sur Seine (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 17/569,955

(22) Filed: Jan. 6, 2022

(65) Prior Publication Data

US 2022/0249357 A1    Aug. 11, 2022

(30) Foreign Application Priority Data

Jan. 29, 2021 (EP) .................................... 21305117

(51) Int. Cl.
| | | |
|---|---|---|
| *A61K 36/00* | (2006.01) | |
| *A61K 8/9789* | (2017.01) | |
| *A61K 8/92* | (2006.01) | |
| *A61Q 19/08* | (2006.01) | |

(52) U.S. Cl.
CPC ............ *A61K 8/9789* (2017.08); *A61K 8/922* (2013.01); *A61K 8/925* (2013.01); *A61Q 19/08* (2013.01); *A61K 2800/805* (2013.01)

(58) Field of Classification Search
CPC ..................................................... C11B 1/104
See application file for complete search history.

(56) References Cited

FOREIGN PATENT DOCUMENTS

| | | | | |
|---|---|---|---|---|
| CN | 101993782 A | * | 3/2011 | ............... C11B 9/02 |
| CN | 105213548 A | | 1/2016 | |
| CN | 109602671 A | | 4/2019 | |
| CN | 109925391 A | | 6/2019 | |
| CN | 111363629 A | | 7/2020 | |
| FR | 2969656 A1 | | 6/2012 | |
| JP | 07309770 A | | 11/1995 | |
| JP | 2003002813 A | | 1/2003 | |
| JP | 2004359640 A | | 12/2004 | |
| JP | 2009073777 A | | 4/2009 | |
| JP | 2014507502 A | | 3/2014 | |

OTHER PUBLICATIONS

Office Action dated Jan. 30, 2023, in corresponding Japanese Application No. 2022-011828, 11 pages.
European Search Report dated Jul. 21, 2021, in European Application No. 21305117; 2 pages.
Notice of Reasons for Rejection dated Jun. 5, 2023, in corresponding Japanese Application No. 2022-011828, 11 pages.

* cited by examiner

*Primary Examiner* — Qiuwen Mi
(74) *Attorney, Agent, or Firm* — Maier & Maier, PLLC

(57) ABSTRACT

An oil extract from *Gardenia jasminoides* flowers obtained by extraction from powder of *Gardenia jasminoides* flowers with supercritical $CO_2$, and the process of obtaining such an extract. Also, cosmetic composition including such an oil extract from *Gardenia jasminoides* flowers having in particular an antiaging effect for the skin, and method for preventing and/or treating changes to the skin due to aging or photoaging using such an extract.

10 Claims, 1 Drawing Sheet

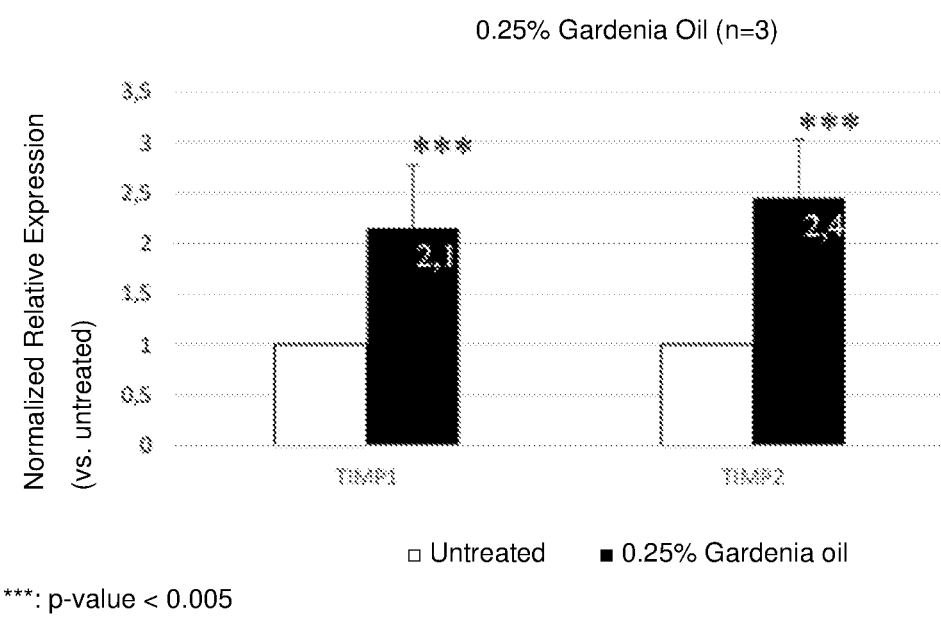

OIL EXTRACT FROM *GARDENIA JASMINOIDES* FLOWERS AND COSMETIC COMPOSITIONS COMPRISING IT

FIELD

The object of the present invention is an oil extract from *Gardenia jasminoides* flowers, characterized in that it can be obtained by extraction from the flowers with supercritical $CO_2$, and also use thereof in cosmetics, for the prevention and/or treatment of alterations of the skin due to, in particular, aging or to age-related physiological mechanisms or to difficulties related to these mechanisms.

BACKGROUND

The skin is mostly made up of three layers, specifically, starting from the outermost surface, the epidermis, dermis and hypodermis.

The outer layer of the skin, the epidermis, is stratified and mainly contributes to providing protection of the skin against external attacks. The dermis is a conjunctive tissue providing both the functions of cohesion and nutrition for the skin.

Cutaneous aging results from two distinct and independent processes which involve intrinsic and extrinsic factors.

The intrinsic or chronobiological aging corresponds to "normal" or physiological aging connected to age.

Extrinsic aging corresponds to aging caused generally by the environment and more specifically the photoaging due to exposure to the sun.

The present invention is interested in intrinsic or physiological skin aging and also extrinsic skin aging.

Skin aging follows a transformation of the conjunctive tissues and the diminishing of the cellular regeneration capacity. This effect is seen by the appearance of fine lines and spots over time. The microcirculation is reduced near the superficial dermis. The macromolecules such as collagen, elastin, and the glycosaminoglycans, one of the constituents of which is hyaluronic acid, are chemically altered. Even the thickness of the dermis regresses, the fibers are degraded and the skin loses the biomechanical and elastic properties thereof. The chemical and enzymatic oxidation phenomena increase with age and lead to the increase of bridging reactions between the fibers such as collagen fibers.

The changes associated with aging may be seen in various ways, among them the following can be mentioned:
  a disorganization of the elastin fibers leading to a loss of firmness, flexibility and elasticity or by the appearance of spider veins;
  the loss of brilliance due to the reduction of the microcirculation and a slowing of cellular renewal near the epidermis and the appearance of fine lines or wrinkles;
  the yellowing of the skin which develops a parchment appearance accompanied by the appearance of pigmented spots associated with a dysfunction of melanin synthesis (melanogenesis);
  Skin drying resulting from a reduction of the barrier function of the horny layer and a slowing of the epidermal renewal.

Because of this, there is a need to provide a polyfunctional active agent which could act on a set of causes of alterations of the skin due to aging and/or to a modification of the age-related physiological mechanisms or related.

Gardenias are plants from the genus *Gardenia*, a genus which comprises about 250 species of flowering plants from the madder family (Rubiaceae), originally from the tropical to subtropical regions of Africa, South Asia, Australasia and Oceania. The extracts, generally aqueous, from these flowers may be sought for use in perfumery.

However, for cosmetic formulations in mostly nonaqueous compositions, like makeup compositions for example, it is desirable to have oil extracts of *Gardenia jasminoides*.

While the oil from the fruit of *Gardenia jasminoides* has already been studied, little scientific research has been done on the extracts from flowers.

The application CN104905999 proposed an oil extract of *Gardenia* flowers for use thereof in perfumes. The oil extract sought is therefore scented, volatile and fragile, and may only be obtained under very gentle conditions of extraction temperature and pressure. The extract described in this application is obtained by extraction from fresh *gardenia* flowers with supercritical $CO_2$ under gentle conditions (35° C./15-MPa) in order to preserve the scented molecules in the extract. Similarly the application FR 2,969,656 seeks to obtain scented extracts from fresh flowers or leaves of various fragile flowers. There again in order to preserve scented molecules during extraction, the method described in the document FR 2,969,656 operates under very gentle pressure conditions (under MPa) and at moderate temperature (under 55° C. and preferably 45° C.)

SUMMARY

The authors of the present invention have now shown, completely surprisingly, that an oil extracted with supercritical $CO_2$ from dried *Gardenia jasminoides* flowers under more forceful temperature and pressure conditions, has an activity on the symptoms due to aging, or age-related physiological mechanisms, or related difficulties with these mechanisms in the epidermis and/or the dermis.

This observation led to perfecting new non-therapeutic cosmetic compositions, more specifically useful for all applications in which it is sought to act on the symptoms due to aging, or on age-related physiological mechanisms, or on the troubles related to these mechanisms near the epidermis and/or the dermis.

Therefore, in a first aspect, the invention relates to a process for preparation of an oil extract of *Gardenia jasminoides* flowers, comprising at least the extraction from powder of *Gardenia jasminoides* flowers with supercritical $CO_2$, at a temperature included between 40 and 80° C., preferably between 43 and 75° C., again preferably between 50 and 70° C., more preferably between 55 and 65° C., and again more preferably between 57 and 62° C. and at a pressure included between 25 and 50 MPa, preferably between 30 and 45 MPa, more preferably between 35 and 45 MPa, they yet more preferably between 40 and 45 MPa.

Such a process does not serve to extract the scent molecules from *Gardenia jasminoides* flowers, since they are destroyed at the claimed pressures and temperatures. Just the same, it does allow the extraction of new unexpected molecules having antiaging properties of cosmetic interest.

The object of the invention is also an oil extract of *Gardenia jasminoides* flowers obtained by such a process. The oil extract of *Gardenia jasminoides* flowers according to the invention is enriched in non-polar molecules such as sterols, in an oil solvent.

According to third aspect, the invention also relates to a cosmetic composition comprising, in a physiologically acceptable medium, at least one oil extract from *Gardenia jasminoides* flowers according to the invention.

Finally, according to a fourth aspect, the object of the invention is the non-therapeutic cosmetic use of an oil extract of *Gardenia jasminoides* flowers such as previously described for the prevention and/or treatment of alterations of the skin due to aging or to photoaging.

BRIEF DESCRIPTION OF THE DRAWINGS

FIG. 1 shows the increase of the expression of genes TIMP1 and TIMP2 in melanocytes after treatment with oil extract from *Gardenia jasminoides* flowers according to the invention at 0.25%.

DETAILED DESCRIPTION

*Gardenia jasminoides*

*Gardenia jasminoides* J. Ellis (synonym *Gardenia florida*) is a genus of flowering plants from the Rubiaceae family.

Evergreen shrub from the Rubiaceae family, like coffee and Tahitian *gardenia*, reaching 0.3 to 3 m high.

The leaves are thick, dark green and shiny.

The *Gardenia* genus comprises about 250 species of flowering plants originally from the tropical to subtropical regions of Africa, South Asia, Australasia and Oceania. *Gardenia jasminoides* is also known under the names *Gardenia angustifolia* Lodd, *Gardenia grandiflora* Lour, *Genipa florida* (L.) Baill, *Genipa grandiflora* (Lour.) Baill, *Jasminum capense* Mill.

The spectacular flowering provides extremely scented and often double flowers with very large white petals, throughout the year in warm climates, from the end of spring to the beginning of summer in cooler climates (March-July).

Depending on the varieties, the white flowers have a scent similar to that of jasmine. *Gardenia jasminoides* is, in fact, also known under the name of Cape Jasmine. *Gardenia jasminoides* is used in traditional Chinese medicine for various properties (emollients, emetics, diuretics, vermifuge, antispasmodics, antiseptics, analgesics). The fruit is an ovoid, yellow or yellow-orange berry containing slightly bent seeds.

The extract according to the invention is obtained from *Gardenia jasminoides* flowers, and preferably from white flowers, in particular from the varieties "Kleim's Hardy" with 5 cm simple flowers and "Crown Jewel" with a 7 cm double flower. Preferably, the *Gardenia jasminoides* flowers used in the invention are cultivated in Gaujacq, France.

The extract of *Gardenia jasminoides* flowers preferably comes in the form of a dispersible dried powder. Dispersible is understood to mean that the powder of *Gardenia jasminoides* flowers comes in dissociated form that can be finely dispersed and for example that the raw material is in particle form and preferably powder. The fresh *Gardenia jasminoides* flowers are, for example, in a first step, separated from the stems and then opened and laid flat on grates. They are then dehydrated under gentle conditions, either in the sun or under vacuum at a temperature of about 40° C. The flowers are preferably dried until reaching a dry matter content over 80% and preferably over 85%.

The flowers are then reduced into dispersible powder by any conventional milling process known to the person skilled in the art, for example at ambient temperature in a cutting mill or, according to a preferred embodiment, by low temperature milling. For low temperature milling, the flowers are preferably cooled to −80° C. and immediately milled in a helical mixer at a temperature included between −20 and −80° C. in order to get a fine and uniform powder. The freezing advantageously serves to assure a better retention of the hydrating properties of the molecules contained in the flowers.

Preferably, the dispersible powder of *Gardenia jasminoides* flowers implemented for the preparation of the extract according to the invention has an average particle size less than 500 μm, preferably less than 300 μm. The powder of *Gardenia jasminoides* flowers has a gentle floral scent and a color ranging from cream white to reddish-brown.

Process for Preparation of an Oil Extract of *Gardenia jasminoides* Flowers

According to an essential aspect of the invention, the oil extract of *Gardenia jasminoides* flowers comprises at least one step of extraction from powder of *Gardenia jasminoides* flowers with supercritical $CO_2$, under specific temperature and pressure conditions.

Effectively, it is to the credit of the applicant for having shown that by proceeding with the oil extraction from *Gardenia jasminoides* flowers with supercritical $CO_2$ under specific temperature and pressure conditions, it was possible to get an extract enriched in non-polar molecules such as sterols, where the extract showed an entirely unexpected effectiveness for combating skin aging and photoaging.

In particular, the extraction with supercritical $CO_2$ is done at a temperature included between 40 and 80° C., preferably between 43 and 75° C., again preferably between 50 and 70° C., more preferably between 55 and 65° C., and again more preferably between 57 and 62° C. and at a pressure included between 25 and 50 MPa, preferably between 30 and 45 MPa, more preferably between 35 and MPa, and yet more preferably between 40 and 45 MPa.

According to a preferred embodiment, the $CO_2$ flow rate is at least 150 g/min, and preferably 200 g/min.

$CO_2$ has the advantage of being inflammable, nontoxic, odorless and easily available because it is a majority component of air.

The extraction with supercritical $CO_2$ is done in the presence of an oil solvent, preferably selected from squalane, 2-ethylhexyl palmitate, caprylic and capric acid triglycerides, and vegetable oils.

The vegetable oil may for example be selected from *camellia* oil, canola oil, sunflower oil, olive oil, sesame oil, apricot kernel oil, grape seed oil, sweet almond oil, safflower oil, hazelnut oil, argan oil, musk-rose oil, common evening primrose oil, borage oil, liquid jojoba wax, and mixtures thereof.

According to a preferred implementation, the extraction with supercritical $CO_2$ is done in the presence of squalane.

It was in fact observed that the addition of squalane during the extraction with supercritical $CO_2$ provided a better solubilization of the molecules of interest present in the *gardenia* flowers. Further, squalane has the advantage of having biomimetic properties with the skin, because it is a natural component of human sebum and forms a hydrolipidic film on the skin. The use of squalane is compatible with the formulation of the extract in a cosmetic composition: it gives the skin a silky effect and penetrates instantly.

According to a specific embodiment, the oil solvent, preferably squalane, is added during the step of extraction with supercritical $CO_2$ in a volume ratio of $CO_2$ to oil solvent included between 200:1 and 50:1.

When about 1 kg of *Gardenia jasminoides* flowers are extracted per batch, the step of extraction with supercritical $CO_2$ is preferably run for a time ranging from 30 minutes to 6 hours, preferably one hour to 3 hours.

In the context of the invention at the end of the step of extraction with supercritical $CO_2$, the pressure may be lowered for the $CO_2$ to change to the gaseous state, in particular to a pressure less than or equal to 7.4 MPa, preferably less than 6 MPa in order to guarantee that all the $CO_2$ has actually returned to the gaseous state.

According to a specific embodiment, the process according to the invention comprises at least the following steps:
 i) drying and milling of fresh *Gardenia jasminoides* flowers;
 ii) extracting from powder of *Gardenia jasminoides* flowers with supercritical $CO_2$ at a temperature included between 40 and 80° C., preferably between 43 and 75° C., again preferably between 50 and 70° C., more preferably between 55 and 65° C., and again more preferably between 57 and 62° C. and at a pressure included between 25 and 50 MPa, preferably between 30 and 45 MPa, more preferably between 35 and 45 MPa, and yet more preferably between 40 and 45 MPa, over for example minutes to 6 hours, preferably in the presence of an oil solvent such as squalane;
 iii) evaporating $CO_2$ by lowering the pressure to 7.4 MPa or less, preferably 6 MPa or less;
 iv) optionally adding an alcohol flow, preferably ethanol, in order to collect the mixture of powder of *Gardenia jasminoides* flowers and solvent, in particular squalane, and then evaporation of said alcohol;
 v) adding an oil solvent, in particular squalane, until the ratio by weight of dried flowers to oil solvent is from 1:5 to 1:20;
 vi) clarifying the oil extract of *Gardenia jasminoides* flowers.

For finishing, the process according to the invention comprises one or several steps for clarification of the oil extract.

Clarification is understood to mean all mechanical separations known to the person skilled in the art. They may for example be selected from filtering, decanting, centrifuging, spinning, or a combination of these techniques.

According to a preferred embodiment, the clarification is done by filtration on a membrane with a porosity less than or equal to 4 μm, or even a 2 μm porosity.

The clarification steps serve to obtain a product that is both substantially clear to the eye and free of suspended microparticles.

According to a particularly preferred embodiment, the process for preparation of the oil extract of *Gardenia jasminoides* flowers according to the invention comprises the following steps:
 i.1) drying *Gardenia jasminoides* flowers in the sun or at 40° C. under vacuum;
 i.2) milling dried flowers and adding them into the basket of the supercritical $CO_2$ extractor;
 ii.1) compressing the carbon dioxide to a pressure equivalent to 45 MPa at laboratory scale or 30 MPa industrial scale;
 ii.2) mixing compressed $CO_2$ with a cosmetic extraction solvent, in particular squalane, according to a ratio by volume of $CO_2$ to squalane of 99:1;
 ii.3) sending the mixture resulting from step i.2 into a heat exchanger in order to reach a temperature of 60° C.;
 ii.4) extracting for at least 1 hour 30 minutes, during which the mixture from step i.2 passes through the basket containing the dried *Gardenia* flowers at a rate of at least 200 g/min such that the extracted molecules diffuse in the mixture;
 iii) depressurizing the supercritical $CO_2$/squalane/*Gardenia* extract mixture in order to reach about 50 bars such that the $CO_2$ becomes a gas again;
 iv.1) sending a flow of ethanol for pushing the squalane/*gardenia* extract mixture and sending the mixture into the collectors of the extraction system;
 iv.2) drawing off the mixture because of the pressure difference between the system and the external environment, so as to get an ethanol/squalane/*Gardenia* extract mixture (since the $CO_2$ evaporated);
 iv.3) evaporating the residual ethanol is done under vacuum;
 v.) adding an oil solvent, in particular squalane, until the ratio by weight of dried flowers to oil solvent is from 1:10; and
 vi) clarifying the oil extract of *Gardenia jasminoides* flowers by filtration through membranes with porosity below 1 μm in order to eliminate possible precipitates.

Oil Extract of *Gardenia jasminoides* Flowers

The invention that is the subject of the present application also covers an oil extract from *Gardenia jasminoides* flowers obtained by means of the previously described process.

An object of the invention is also an oil extract of *Gardenia jasminoides* flowers enriched in non-polar molecules such as sterols.

Cosmetic Composition

Another object of the present invention is a cosmetic composition comprising, in a physiologically acceptable medium, at least one oil extract from *Gardenia jasminoides* flowers.

The composition implemented according to the invention generally comprises, in addition to the previously described extract, a physiologically acceptable and preferably cosmetically acceptable medium, meaning it is suitable to use in contact with human skin without risk of toxicity, incompatibility, instability, allergic response and in particular that it does not cause uncomfortable sensations (redness, tightness, tingling).

Advantageously, said cosmetic or dermatological composition may come in the form of a powder, emulsion, microemulsion, nanoemulsion, suspension; of a lotion, cream, aqueous gel or hydro-alcoholic solution; foam, serum, solution or dispersion for aerosol; or dispersion for lipidic vesicles.

In the case of an emulsion, it may be an oil-in-water or water-in-oil emulsion.

The cosmetic or dermatological composition according to the invention may also comprise a solvent selected based on various ingredients and the form of administration.

The following can be mentioned as examples: water (preferably demineralized water or floral waters), an alcohol such as ethanol.

Said cosmetic composition may also comprise, in addition to the extract according to the invention:
 at least one additive typical in the field, such as for example at least one compound selected from an emollient or humectant, a gelling agent and/or a thickener, a surfactant, an oil, an active ingredient, coloring, a preservative, an antioxidant, an active ingredient, an organic or inorganic powder, a sunscreen and a scent.
 one or more humectants, such as polyols (glycerin, diglycerin, propylene glycol, caprylyl glycol, pentylene glycol, hexanediol), sugars, glycosaminoglycans such as hyaluronic acid and salts and esters thereof; and the polyquaterniums such as lipidure PMB. Said humectant will be present in the composition at a concentration of order 0 to 30%, preferably 0.005 to 10% by total weight of the composition.

- one or more emollients which may be selected for example from esters such as jojoba esters, fatty acid and fatty alcohol esters (octyldodecyl myristate, trimethylhexanoin, dicaprylyl carbonate, isostearyl isostearate, caprylic/capric triglyceride), butters such as Shea butter (butyrospernum parkii butter extract, shea butter ethyl esters, sold under the names LIPEX SHEASOFT, LIPEX SHEA-U, LIPEX SHEA, LIPEX SHEALIGHT, LIPEX SHEA TRIS) or moringa (moringa oil/hydrogenated moringa oil esters), waxes (*Acacia decurrens* flower wax & *Helianthus annuus* cera seed wax, $C_{10}$-$C_{18}$ triglycerides), vegetable oils, phytosqualane, and alkanes (undecane, tridecane). Said emollient will be present in the composition at a concentration of order 0.1 to 30%, preferably 0.5 to 10% by total weight of the composition.
- one or more gelling agents and/or thickeners for the aqueous phase, selected for example from cellulose derivatives, gums of vegetable origin (guar, carob, alginates, carrageenans, pectins), microbial origin (xanthine), clays (laponite), homo- and co-polymers crosslinked or not, hydrophilic or amphiphilic, acryloylmethylpropane sulfonic acid (AMPS) and/or acrylamide and/or acrylic acid and/or salts or esters of acrylic acid (sold under the names ARISTOFLEX AVC, Aristoflex AVS, Aristoflex HMB, SIMULGEL NS, Simulgel EG, Simulgel 600, Simulgel 800, Pemulen, carbopol, Sepiplus 400, Seppimax zen, Sepiplus S, COSMEDIA SP). Said gelling agent and/or thickener will be present in the composition at a concentration of order 0.1 to 10% by total weight of the composition.
- One or more surfactants, such as lecithins, polyglycerol derivatives, sugar derivatives (the derivatives of glucosides or xylosides sold under the name MONTANOV 68, MONTANOV 202, Montanov 82, MONTANOV L, EASYNOV), phosphates ($C_{20}$-$C_{22}$ alkyl phosphates sold under the name SENSANOV WR). Said surfactant will be present at a concentration of order 0.1 to 8%, preferably 0.5 to 3% by weight relative to the total weight of the composition.
- one or more active ingredients of natural, biotechnological or synthetic origin having a biological activity and having an effectiveness on the skin via biological sites, for example selected from vitamins such as vitamin C and derivatives thereof (ascorbyl glucoside, 3-o-ethyl ascorbic acid, ascorbyl tetraisopalmitate), vitamin A and derivatives thereof, vitamin E and derivatives thereof, vitamin B3 or niacinamide, panthenol, oligoelements, allantoin, adenosine, peptides (Palmitoyl tetrapeptide-7, Palmitoyl Tripeptide-1, Palmitoyl Pentapeptide-4, Acetyl Dipeptide-1 Cetyl Ester, Acetyl Tetrapeptide-5 sold under the name NP RICIN, MATRIXYL 3000, IDEALIFT, EYESERYL), vegetable extracts (*Glycyrrhiza glabra* extract, *Centella asiatica* leaf extract, *Secale cereale* seed extract), yeast extracts, alpha hydroxy acids such as glycolic or lactic acid, tranexamic acid and derivatives thereof such as cetyl tranexamic ester, etc. Said active ingredient will be present in the composition at a concentration of order 0.1 to 10% by total weight of the composition.

Other additives typically used in cosmetics may also be present in the composition according to the invention, in particular preservatives, antioxidants or scents well known in the technical field.

The person skilled in the art is able to select, from the set of possible additives, both the kind and the quantity of those which will be added to the composition, such that the composition will retain all the properties thereof.

An object of the invention is also the cosmetic use of the oil extract of *Gardenia jasminoides* flowers for preventing and/or treating changes to the skin due to aging or photoaging.

In particular the oil extract of *Gardenia jasminoides* flowers may be used to confer a smoothing antiaging effect.

In this embodiment, the extract or the composition is applied to the altered but not pathological skin.

Another object of the invention is the non-therapeutic cosmetic use of an oil extract of *Gardenia jasminoides* flowers such as previously described as an agent inhibiting the activity of matrix metalloproteinases (MMPs).

Finally the invention targets the non-therapeutic cosmetic use of an oil extract of *Gardenia jasminoides* flowers such as previously described, as an agent stimulating cellular metabolism, in particular stimulating the expression of TIMP 1 and/or TIMP 2 genes.

The invention will now be illustrated by the following nonlimiting examples.

Example: Activation of Two MMP Inhibitors in Normal Human Melanocytes Treated with Oil Extract of *Gardenia jasminoides*

Preparation of the Extract:

An oil extract of *Gardenia jasminoides* according to the invention was prepared according to the following steps:

a) The freshly collected flowers are dried in the sun or at 40° C. under vacuum in order to preserve their quality and then finely milled.
b) The milled flowers are arranged in the basket of the supercritical $CO_2$ extractor.
c) Carbon dioxide ($CO_2$) is compressed to a pressure equivalent to 450 bars a laboratory scale or 300 bars at industrial scale.
d) The compressed $CO_2$ is then mixed with a cosmetic solvent, squalane, according to a ratio of 99:1 ($CO_2$:squalane, by volume).
e) The mixture is sent into a heat exchanger in order to reach a temperature of 60° C.
f) For at least 1 hour 30 minutes, the mixture passes through the basket containing the dried *gardenia* flowers at a rate of at least 200 g/min; the extracted molecules diffuse in the mixture.
g) The supercritical $CO_2$/squalane/*gardenia* extract mixture is then depressurized to lower the pressure to about 50 bars; the $CO_2$ becomes a gas again.
h) A flow of ethanol is sent at this point for pushing the squalane/*gardenia* extract mixture and sending the mixture into the collectors of the extraction system.
i) The mixture is drawn off because of the pressure difference between the system and the external environment, an ethanol/squalane/*Gardenia* extract mixture (since the $CO_2$ evaporated) results.
j) The residual ethanol is evaporated under vacuum.
k) As much squalane as necessary is re-added so that the final mass of the extract is 10 times greater than the mass of plant used (e.g. for 100 g of dried flowers used, add 1000 g of squalane).
l) The extract is filtered on a 1 μm membrane in order to eliminate possible precipitates.

Protocol:

Normal human epidermal melanocytes coming from three different donors were cultivated on six-well plate in M254 medium supplemented with 1% HMGS for 72 hours at 37° C. and 5% $CO_2$. At 70% confluency, the cells were incubated or not (untreated condition) for 24 hours with a non-cytotoxic concentration (0.25%) of prepared oil extract of *Gardenia jasminoides*. Each condition was done in duplicate. The total RNA was extracted by using the RNeasy 96 Plate Extraction kit (Qiagen) according to the supplier's recommendations. The quantity and quality of the RNA were evaluated by means of a spectrophotometer (Multiskan GO, Thermo Fisher). The complementary DNA was then synthesized from an RNA microgram according to the procedure described by the supplier (iScript SUPER mix, Biorad) and used in order to determine the level of expression of genes of interest by quantitative PCR. The analysis was done by the method of comparison of the Ct after normalization relative to the expression of reference genes, by using the Biorad Maestro CFX software.

Results:

The results obtained after treatment of melanocytes by oil extract of *Gardenia jasminoides* according to the invention (GO) are shown in FIG. 1. Significant increase of the expression of the TIMP 1 and TIMP 2 genes (Tissue Inhibitor of Metalloproteinase) was observed in melanocytes treated with 0.25% GO relative to untreated melanocytes. The treated melanocytes thus expressed on average (n=3) 2.15 times more TIMP1 and 2.45 times more TIMP2 than untreated melanocytes.

| INCI Name | (% by weight) |
|---|---|
| LIMNANTHES ALBA (MEADOWFOAM) SEED OIL | 1-10 |
| BUTYROSPERMUM PARKII BUTTER (LIPEX SHEASOFT) | 1-10 |
| BUTYROSPERNUM PARKII BUTTER EXTRACT (LIPEX SHEA TRIS) | 1-10 |
| CAMELLIA OLEIFERA SEED OIL | 1-10 |
| CETYL ETHYLHEXANOATE | 1-5 |
| SQUALANE | |
| SODIUM ACRYLATES COPOLYMER & LECITHIN | 0.1-5 |
| ACRYLATES/C10-30 ALKYL ACRYLATE CROSSPOLYMER | 0.1-2 |
| GLYCERYL STEARATE & PEG-100 STEARATE | 0.1-5 |
| XANTHAN GUM | 0.01-5 |
| HYDROXYETHYL CELLULOSE | 1-10 |
| SILICA | 0.1-10 |
| SODIUM HYALURONATE | 0.01-3 |
| GLYCERIN | 1-30 |
| POLYQUATERNIUM-51 | 1-10 |
| ADENOSINE | 0.1-0.5 |
| NIACINAMIDE | 0.1-5 |
| PALMITOYL TETRAPEPTIDE-7 | 1-5 |
| TRANEXAMIC CETYL ESTER | 0.001-5 |
| ALLANTOINE | 0.001-5 |
| TOCOPHERYL ACETATE | 0.1-5 |
| EXTRACT ACCORDING TO THE INVENTION | 0.001-10 |
| YEAST EXTRACT | 0.1-5 |
| GLYCYRRHIZA GLABRA EXTRACT | 0.1-5 |
| ASCORBYL GLUCOSIDE | 0.001-5 |
| GLYCOLS (CAPRYLYL GLYCOL AND/OR | 0.1-10 |

| | | DONOR 1 | | | DONOR 2 | | | DONOR 3 | | |
|---|---|---|---|---|---|---|---|---|---|---|
| Target | Condition | Average CT | Normalized relative expression | p-Value | Average CT | Normalized relative expression | p-Value | Average CT | Normalized relative expression | p-Value |
| TIMP1 | 0.25% OG | 22.80 | 2.07887 | 0.001588 | 25.88 | 156515 | 0.002353 | 22.01 | 2.80538 | 0.001649 |
| | Untreated | 25.65 | 1.00000 | | 27.89 | 1.00000 | | 25.98 | 1.00000 | |
| TIMP2 | 0.25% OG | 22.36 | 2.82179 | 0.001940 | 23.69 | 1.78326 | 0.005172 | 19.89 | 2.74187 | 0.003784 |
| | Untreated | 25.69 | 1.00000 | | 25.88 | 1.00000 | | 28.82 | 1.00000 | |

There are four members of the TIMP family (TIMP1 to 4) that act as specific inhibitors of the activity of the matrix metalloproteinases (MMPs). MMPs are known to be involved in the breakdown of the extracellular matrix of the dermis and aging of the skin. In particular, following exposure to UV rays, a high production of MMPs is observed, which contributes to cutaneous photoaging. Now, it was shown that the melanocytes have a very high proteolytic activity, by secreting in particular MMPs. Thus, the oil extract of *Gardenia jasminoides* flowers according to the invention could inhibit the activity of MMPs by stimulating the expression of the TIMP in the melanocytes and therefore participating in preventing and/or treating aging and/or photoaging by a smoothing antiaging effect, for example.

Example: Cosmetic Composition

The following compositions may be prepared conventionally for the person skilled in the art. The quantities indicated below are expressed in percentages by weight. The ingredients in all capital letters are identified according to the INCI name.

A—Oil/Water Emulsion

-continued

| INCI Name | (% by weight) |
|---|---|
| PENTYLENE GLYCOL AND/OR BUTYLENE GLYCOL AND/OR PROPANEDIOL) | |
| WATER | Qs 100 |

B—Oil/Water Emulsion Cream

| INCI Name | (% by weight) |
|---|---|
| BEHENYL ALCOHOL | 1-5 |
| CETYL ALCOHOL | 0.1-5 |
| LAUROYL LYSINE | 1-5 |
| CAMELLIA OLEIFERA SEED OIL | 1-10 |
| CETYL ETHYLHEXANOATE | 1-5 |
| SQUALANE | 1-10 |
| HYDROGENATED LECITHIN & GLYCINE SOJA (SOYBEAN) STEROLS | 1-5 |
| POLYGLYCERYL-6 POLYHYDROXYSTEARATE (AND) POLYGLYCERYL-6 POLYRICINOLEATE | 1-7 |
| XANTHAN GUM | 0.01-2 |
| AGAR | 0.1-5 |
| ADENOSINE | 0.1-0.5 |
| NIACINAMIDE | 0.1-5 |
| SECALE CEREALE (RYE) SEED EXTRACT | 0.1-5 |
| PALMITOYL TETRAPEPTIDE-7 | 1-5 |

-continued

| INCI Name | (% by weight) |
|---|---|
| TRANEXAMIC CETYL ESTER | 0.001-5 |
| ASCORBYL GLUCOSIDE | 0.001-5 |
| YEAST EXTRACT | 1-3 |
| SACCHARIDE ISOMERATE | 1-5 |
| EXTRACT ACCORDING TO THE INVENTION | 0.001-10 |
| GLYCYRRHIZA GLABRA EXTRACT | 0.001-5 |
| WATER | Qs 100 |

These compositions may be applied to the skin every day, morning and/or evening.

The invention claimed is:

1. A process for preparation of a cosmetic oil extract of *Gardenia jasminoides* flowers, comprising at least extracting from powder of dried *Gardenia jasminoides* flowers with supercritical $CO_2$, at a temperature included between 40 and 80° C. and at a pressure included between 25 and 50 MPa, wherein the *Gardenia jasminoides* flowers are dried by being dehydrated either under the sun or under vacuum at a temperature of about 40° C.

2. The process according to claim 1, wherein the extraction with supercritical $CO_2$ is done in the presence of an oil solvent selected from the group consisting of squalane, 2-ethylhexyl palmitate, caprylic and capric acid triglycerides, and vegetable oils.

3. The process according to claim 2, wherein the oil solvent is added in a volume ratio of $CO_2$ to oil solvent included between 200:1 and 50:1.

4. The process according to claim 1, wherein the powder of *Gardenia jasminoides* flowers is obtained by further milling of dried *Gardenia jasminoides* flowers.

5. The process according to claim 1, wherein at the end of the step of extraction with supercritical $CO_2$, the pressure may be lowered for the $CO_2$ to change to the gaseous state to a pressure less than or equal to 7.4 MPa.

6. The process according to claim 1, wherein the process comprises at least the following steps:
    i) drying *Gardenia jasminoides* flowers either under the sun or under vacuum at a temperature to obtain dried *Gardenia jasminoides* flowers; milling the dried *Gardenia jasminoides* flowers to obtain a powder of *Gardenia jasminoides* flowers;
    ii) extracting the powder of *Gardenia jasminoides* flowers with supercritical $CO_2$ at a temperature included between 40 and 80° C. and at a pressure included between 25 and 50 MPa, over 30 minutes to 6 hours, in the presence of an oil solvent, with a ratio by weight of dried powdered flowers to oil solvent from 1:5 to 1:20;
    iii) evaporating $CO_2$ by lowering the pressure to 7.4 MPa or less;
    iv) optionally adding an alcohol flow in order to collect the mixture of powder of *Gardenia jasminoides* flowers and solvent, and then evaporation of said alcohol to obtain an oil extract of *Gardenia jasminoides* flowers; and
    v) clarifying the oil extract of *Gardenia jasminoides* flowers.

7. The process according to claim 6, wherein the step v) of clarification is done by filtration on a membrane with a porosity below 1 µm.

8. A cosmetic oil extract of *Gardenia jasminoides* flowers obtained by the process according to claim 1.

9. A cosmetic composition comprising, in a physiologically acceptable medium, at least one cosmetic oil extract from *Gardenia jasminoides* flowers according to claim 8.

10. A method for treating or reducing the incidence of changes to a subject's skin due to aging or photoaging, comprising applying to the subject's skin the cosmetic oil extract of *Gardenia jasminoides* flowers obtained by the process according to claim 1 or a cosmetic composition comprising, in a physiologically acceptable medium, said cosmetic oil extract according to claim 1.

* * * * *